United States Patent [19]

Stuart

[11] Patent Number: 5,044,766

[45] Date of Patent: Sep. 3, 1991

[54] METHOD AND APPARATUS FOR DETERMINING THE THERMAL TIME CONSTANT OF FINE METAL WIRE SEGMENTS

[75] Inventor: James G. Stuart, Mont Clare, Pa.

[73] Assignee: Calspan Corporation, Buffalo, N.Y.

[21] Appl. No.: 562,174

[22] Filed: Aug. 3, 1990

[51] Int. Cl.⁵ .............................................. G01N 25/20
[52] U.S. Cl. ........................................ 374/43; 374/44;
324/105; 324/71.1; 73/204.14; 364/481;
364/487
[58] Field of Search ..................... 374/43, 44, 29, 169,
374/170, 32, 45; 364/483, 484, 487, 485, 480,
481, 556; 340/870.17; 324/104, 105, 127, 71.1;
73/204.14, 204.15, 204.18

[56] References Cited

U.S. PATENT DOCUMENTS

| | | |
|---|---|---|
| 4,630,938 | 12/1986 | Piorkowska-Palczewska et al. ........................................... 374/44 |
| 4,728,887 | 3/1988 | Davis .................................... 324/127 |
| 4,888,987 | 12/1989 | Zhang ................................ 374/43 X |

FOREIGN PATENT DOCUMENTS 0621995 8/1978 U.S.S.R. .............................. 374/44
0693196 10/1979 U.S.S.R. .............................. 374/44

Primary Examiner—Stuart S. Levy
Assistant Examiner—Joseph A. Rhoa
Attorney, Agent, or Firm—Biebel & French

[57] ABSTRACT

The thermal time constant of fine metal wire segments, such as those used to initiate explosive reactions, is measured by passing a variable frequency source of current through the wire. The magnitudes of the sine and cosine components of the third harmonic of the voltage developed across the wire are detected and compared to each other to provide a control signal which is applied to the frequency source to change the its frequency in a direction which tends to make those components equal in magnitude. The magnitude of the control signal, when the third harmonic sine and cosine components are equal, is displayed as a function of the thermal time constant of the wire segment.

3 Claims, 1 Drawing Sheet

METHOD AND APPARATUS FOR DETERMINING THE THERMAL TIME CONSTANT OF FINE METAL WIRE SEGMENTS

BACKGROUND OF THE INVENTION

This invention relates to the non-destructive measurement of the thermal time constant of fine metal wire segments, especially wire segments of the type used to initiate explosive reactions.

Many explosive and pyrotechnic devices are detonated by the heat generated when a large electrical signal is passed through a metal wire segment embedded in the device. The non-destructive testing of these wire segments is important to ensure the continued reliability and readiness of devices already built and to confirm that wire segments yet to be installed are capable of accomplishing their task.

The prior art technique for the non-destructive testing of the thermal time-constant of fine (i.e. small, thin) wires, first developed in 1959, is carried out with a testing apparatus that includes a constant-current source which is switched on suddenly to pass a small current through the wire (a current of such small magnitude that it would not destroy the wire or generate sufficient heat to detonate the device), and then recording the voltage developed across the wire as a function of time. The data recorded is then compared with an exponential curve to provide some indication of the thermal time constant of the wire under test. Unfortunately, this method is cumbersome, it ought to be performed by a skilled operator, and it gives results of inconsistent validity.

Accordingly, there remains a need for a simple and reliable method and apparatus for testing fine wire segments.

SUMMARY OF THE INVENTION

The present invention provides a simple method and apparatus for measuring the thermal time-constant of fine metal wire segments. A variable frequency source of current is passed through the wire and the third harmonic of both the sine and cosine components of the voltage developed across the wire as the current from said variable frequency source passes therethrough is detected. The magnitude of said third harmonic sine and cosine components are compared against each other and a control signal is generated which, when applied to the variable frequency source of current, changes the frequency thereof in a direction which tends to make said components equal in magnitude. The magnitude of said control signal when said third harmonic sine and cosine components are equal is displayed directly as a function of the thermal time constant of the metal wire.

Specifically, the frequency of a variable frequency oscillator, which is the source of current to the wire, is trippled and one output is phase shifted 90 degrees. These two signals are applied to a pair of synchronous detectors which sense the voltage developed across the wire. Thus, the third harmonic of the developed voltage is being detected. The outputs of the synchronous detectors are compared and a feedback signal is developed to control the frequency of the oscillator. The magnitude of the control signal is directly related to the thermal time constant of the wire under test.

The method and apparatus are straight forward easy to operate while giving accurate and repeatable results.

Accordingly, it is an object of this invention to provide an apparatus for measuring the thermal time-constant of fine metal wire segments comprising means for supplying a variable frequency source of current to the wire, means for sensing the sine and cosine components of the third harmonic of the voltage developed across the wire as the current from said variable frequency source passes therethrough, means comparing the magnitude of said third harmonic sine and cosine components for providing a control signal which, when applied to said variable frequency source of current, changes the frequency thereof in a direction which tends to make said components equal in magnitude, and means for displaying the magnitude of said control signal when said third harmonic sine and cosine components are equal as a function of the thermal time constant of the metal wire.

It is a further object of this invention to provide a method of determining the thermal time-constant of fine metal wire segments comprising the steps of passing a variable frequency source of current through the wire, sensing the voltage developed across the wire as the current from said variable frequency source passes therethrough, sensing the third harmonic of both the sine and cosine components of said developed voltage, comparing the magnitudes of said third harmonic sine and cosine components, providing a control signal to the voltage variable frequency source of current of such character which tends to make said third harmonic sine and cosine components equal in magnitude, and displaying the value of said control signal when said third harmonic sine and cosine components are equal as a function of the thermal time constant of the metal wire.

Other objects and advantages of the invention will be apparent from the following description, the accompanying drawings and the appended claims.

DESCRIPTION OF THE PREFERRED EMBODIMENT

Figure 1:
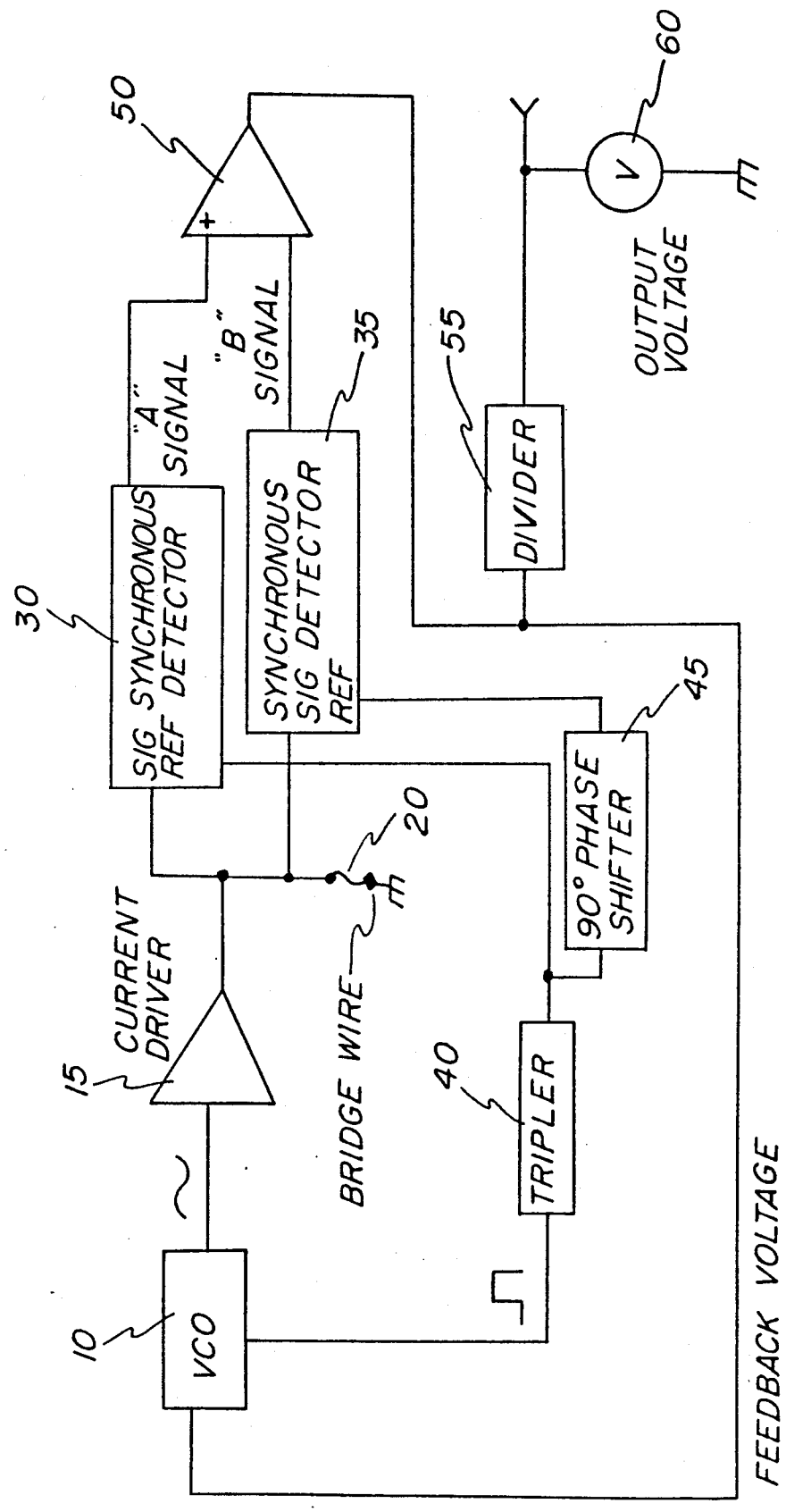
FIG. 1 is an electrical block diagram showing the components which comprise a preferred embodiment of the invention.

The present invention takes advantage of some well know physical properties of small metal wires. For example, it is well known that such wires are heated by electric current flowing through it and that the wire temperature will be a function of input power. That function may be expanded in a Taylor series of form $$dT/dt = \sum_{n=0}^{\infty} C_n P^n + \text{other terms},$$

where T is the temperature rise, t is time, P is equal to power, and C is a coefficient.

Because so little energy is introduced into the wire, the temperature-rise will be so small that the second and succeeding terms in this expansion are negligible. That leaves only the first term, which predicts a temperature rise proportional to power. To this is added a dissipation term proportion to the difference between the temperature of the wire and room temperature, T, in order to make thermal equilibrium possible. Thus, the heating of the wire may be described by $$dT/dt = P/c_p - T/X \quad \text{Equation 1}$$

where
- T = (wire temperature - room temperature)
- t = time
- P = electrical power dissipated in the wire
- $c_p$ = heat capacity of the wire at constant pressure
- X = thermal time-constant characterizing the wire's shape and immediate environment.

It is the thermal time-constant X that is of immediate interest, and the following analysis will illustrate how the differential equation (Equation 1) will be solved.

If the current passing through the wire is known, and the voltage across the wire is measured, then the resistance of the wire can be inferred from the following equation:

$$R = V/I \quad \text{Equation 2}$$

where V is voltage, I is current, and R is resistance.

The resistance of the wire, R, depends on the wire's temperature, as shown in Equation 3. Thus, temperature can be determined.

$$R = R_o + aT \quad \text{Equation 3}$$

where
- $R_o$ = resistance of wire at room temperature, and
- a = the wire's thermal coefficient of resistance.

Since both power (the product of voltage and current) and temperature are known as functions of time, Equation 1 may then be solved for the thermal time-constant.

The general procedure outlined above, whose purpose is to solve the differential equation, can be followed in a number of different ways, of which the two most important will be called here, respectively, the "time-domain approach" and the "frequency-domain approach". The time-domain approach is represented by the prior art and uses the complicated, bulky, expensive apparatus previously described. The frequency-domain approach is without inherent inaccuracies or requirements for complicated equipment.

In the frequency-domain approach, a sinusoidal current given by Equation 4 is made to flow through the wire.

$$I = I_o \sin wt \quad \text{Equation 4}$$

where $I_o$ is the amplitude of current, w is the angular frequency of oscillator, and t is time.

The instantaneous power P(t) dissipated in the wire is given by Equation 5.

$$P(t) = I^2 R$$
$$= (I_o \sin wt)^2 (R_o + aT) \quad \text{Equation 5}$$

When the power from Equation 5 is substituted into Equation 1, the differential equation becomes soluble. A trial solution of the form given by Equation 6 is used. The coefficients can be determined if all terms containing second or higher powers of T (the difference between wire temperature and ambient) are dropped, which is consistent with the original assumption that T is very small.

$$T = T' + T''(\sin 2wt + Z) \quad \text{Equation 6}$$

where Z is an unimportant phase constant.

The solution, Equation 6, is substituted into Equation 3 to get the resistance as a function of time. This then is multiplied by the current Equation 4 to get the voltage across the wire as a function of time. This takes the form given in Equation 7.

$$V = V' \sin(wt + Q) + V'' \cos(3wt + f) \quad \text{Equation 7}$$

where Q is an unimportant constant, and f is the phase.

The second term of Equation 7 can easily be detected by a phase detector tuned to the third harmonic of the fundamental frequency. The phase f, the quantity that is measured, is given by Equation 8.

$$f = \tan^{-1}(\tfrac{1}{2}Xw) \quad \text{Equation 8}$$

If the driving frequency is automatically adjusted to make the phase f equal to forty-five degrees, then the thermal time-constant is simply given by Equation 9 where the drive frequency is known.

$$X = \tfrac{1}{2}w \quad \text{Equation 9}$$

An apparatus for measuring the thermal time-constant by the frequency-domain approach is shown in the block diagram of FIG. 1. Synchronous (or lock-in) detection is used to eliminate the fundamental-frequency component of the signal.

The circuit includes a variable frequency oscillator 10 and a current driver 15 which together provide the means for supplying a variable frequency source of current to a wire 20 undergoing testing. The voltage developed across wire 20 is sensed by a pair of synchronous detectors 30 and 35. A reference signal for the detectors 30 and 35 is developed by a frequency tripler 40, which is responsive to the actual frequency output of the frequency source or oscillator 10. The detector 30 receives its reference input directly from the tripler 40 while the detector 35 receives its input from a 90 degree phase shifter circuit 45.

Thus, the circuits 30, 35, together with the frequency reference circuits 40 and 45, comprise means for sensing the third harmonic of both the sine and cosine components of the voltage developed across the wire as the current from said variable frequency source passes therethrough. The fundamental frequency of the oscillator 10 is ignored; only the third harmonic of the voltage developed across the wire 20 will be detected.

Feedback circuit means, responsive the outputs of said synchronous detector means, apply a control signal in the form of a control voltage to the voltage variable frequency source or oscillator 10 in a direction which tends to make the magnitude of the outputs of said synchronous detector means equal. Comparator means or differential amplifier 50 compares the magnitude of said third harmonic sine component from detector 30 with the third harmonic of the cosine component from detector 35 and provides a control signal output or feedback voltage to the oscillator 10 in a direction which tends to make said components equal in magnitude and thus to make the phase f given by Equation 8 have a value of exactly 45 degrees.

A voltage indicator circuit, including a divider 55 and voltmeter 60 comprise means for displaying value of said control voltage as a function of the thermal time constant of the metal wire. The divider 55 produces a DC output voltage that is simply proportional to the thermal time-constant.

The outputs of detectors 30 and 35 are proportional to the cosine and to the sine, respectively, of the phase given in Equation 8. The differential amplifier 50 adjusts the frequency of the oscillator 10 to make these outputs equal in magnitude. When this is achieved, the phase is equal to forty-five degrees and Equation 9 then provides the value of the thermal time-constant of the wire 20. The DC feedback voltage is proportional to the frequency of the oscillator 10, and therefore by Equation 9, it is proportional to the inverse of the thermal time constant.

Thus, a simple, automatic, accurate and reliable method and apparatus for measuring the thermal time constant of fine metal wires has been described.

While the method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claim.

What is claimed is:

1. Apparatus for measuring the thermal time-constant of fine metal wire segments comprising means for supplying a variable frequency source of current to the wire, means for sensing the sine and cosine components of the third harmonic of the voltage developed across the wire as the current from said variable frequency source passes therethrough, means comparing the magnitude of said third harmonic sine and cosine components for providing a control signal which, when applied to said variable frequency source of current, changes the frequency thereof in a direction which tends to make said components equal in magnitude, and means for displaying the magnitude of said control signal when said third harmonic sine and cosine components are equal as a function of the thermal time constant of the metal wire.

2. Apparatus for measuring the thermal time-constant of fine metal wire segments comprising means for supplying a voltage variable frequency source of current to the wire, frequency tripler means responsive to the actual frequency output of said frequency source means for phase shifting the output of said tripler means by 90 degrees, first and second synchronous detector means sensing the voltage developed across the wire, said first detector means receiving a reference input from said tripler means and said second detector means receiving a reference input from said phase shifting means, feedback circuit means responsive the outputs of said synchronous detector means for applying a control voltage to said voltage variable frequency source in a direction which tends to make the magnitude of the outputs of said synchronous detector means equal, and means for displaying value of said control voltage as a function of the thermal time constant of the metal wire.

3. Method of determining the thermal time-constant of fine metal wire segments comprising the steps of passing a variable frequency source of current through the wire, sensing the voltage developed across the wire as the current from said variable frequency source passes therethrough, sensing the third harmonic of both the sine and cosine components of said developed voltage, comparing the magnitudes of said third harmonic sine and cosine components, providing a control signal to the voltage variable frequency source of current of such character which tends to make said third harmonic sine and cosine components equal in magnitude, and displaying the value of said control signal when said third harmonic sine and cosine components are equal as a function of the thermal time constant of the metal wire.

* * * * *